United States Patent [19]
Duckworth et al.

[11] Patent Number: 6,100,062
[45] Date of Patent: Aug. 8, 2000

[54] EXPRESSION SYSTEM FOR HSCLOCK

[75] Inventors: David Malcolm Duckworth, Bishop's Stortford; David Michalovich, Crouch End, both of United Kingdom

[73] Assignee: SmithKline Beecham plc, Brentford, United Kingdom

[21] Appl. No.: 09/107,847

[22] Filed: Jun. 30, 1998

[51] Int. Cl.[7] ............................ C12P 21/06; C07H 17/00; C07K 14/00
[52] U.S. Cl. ...................... 435/69.1; 435/325; 435/250.3; 435/320.1; 536/23.1; 530/350
[58] Field of Search ..................................... 435/435, 325, 435/320.1, 253.2; 536/23.1; 530/350

[56] References Cited

U.S. PATENT DOCUMENTS 5,874,241  2/1999  Takahashi et al. ...................... 435/69.1

OTHER PUBLICATIONS

GenBank Accession No. AB002332.
GenBank Accession No. AF000998.
King, David P., et al., "Positional Cloning of the Mouse Circadian *Clock* Gene", Cell, vol. 89:641–653 (1997).
Nagase, Takahiro, et al., "Prediction of the Coding Sequences of Unidentified Human Genes. VII. The Complete Sequences of 100 New cDNA Clones from Brain Which Can Code for Large Proteins in vitro", DNA Research vol. 4:141–150 (1997).
Dunlap, Jay C., et al., "Genetic and Molecular Analysis of Circadian Rhythms", Annual Review Genet., vol. 30:579–601 (1996).
Antoch, Marina P., et al., "Functional Identification of the Mouse Circadian *Clock* Gene by Transgenic BAC Rescue", Cell, vol. 89:655–667 (1997).
Hall Jeffrey C., "Tripping along the trail to the molecular mechanisms of biological clocks", Trends Neurosci., vol. 18:230–240 (1995).

*Primary Examiner*—Karen Cochrane Carlson
*Attorney, Agent, or Firm*—William T. Han; Ratner & Prestia; William T. King

[57] ABSTRACT

The use of HSCLOCK polypeptides and polynucleotides in the design of protocols for the treatment of sleep disorders, jet lag, pathologies that occur in advanced age, among others, and diagnostic assays for such conditions. Also disclosed are methods for producing such polypeptides by recombinant techniques.

5 Claims, No Drawings

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
    (A) LENGTH: 5715 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:1:

```
AGCTGATTCT ATCACATTGT AAGATGCCTT TGGATAATTC TACAGTCCTC TTAAATGAAT        60

CTTTAGAACT TGGCAAGTCT CACTAGATAC CTTCAATCAT CATTTTGAGC TCAAAGAATT       120

CTGAGACTTA TGGTTGGTCA TATAGAAGAG GACCTTGAAC CTATAGTTTC CTGAAGAATC       180

AGTTTAAAAG ATCCAAGGAG TACAAAAGGA GAAGTACAAA TGTCTACTAC AAGACGAAAA       240

CGTAGTATGT TATGTTGTTT ACCGTAAGCT GTAGTAAAAT GAGCTCGATT GTTGACAGAG       300

ATGACAGTAG TATTTTTGAT GGGTTGGTGG AAGAAGATGA CAAGGACAAA GCGAAAAGAG       360

TATCTAGAAA CAAATCTGAA AAGAAACGTA GAGATCAATT TAATGTTCTC ATTAAAGAAC       420

TGGGATCCAT GCTTCCTGGT AATGCTAGAA AGATGGACAA ATCTACTGTT CTGCAGAAAA       480

GCATTGATTT TTTACGAAAA CATAAAGAAA TCACTGCACA GTCAGATGCT AGTGAAATTC       540

GACAGGACTG GAAACCTACA TTCCTTAGTA ATGAAGAGTT TACACAATTA ATGTTAGAGG       600

CTCTTGATGG TTTTTTTTTA GCAATCATGA CAGATGGAAG CATAATATAT GTGTCTGAGA       660

GTGTAACTTC ATTACTTGAA CATTTACCAT CTGATCTTGT GGATCAAAGT ATATTTAATT       720

TTATCCCAGA AGGGGAACAT TCAGAGGTTT ATAAAATACT CTCTACTCAT CTGCTGGAAA       780

GTGATTCATT AACCCCAGAA TATTTAAAAT CAAAAAATCA GTTAGAATTC TGTTGTCACA       840

TGCTGCGAGG AACAATAGAC CCAAAGGAGC CATCTACCTA TGAATATGTA AAATTTATAG       900

GAAATTTCAA ATCTTTAAAC AGTGTATCCT CTTCAGCACA CAATGGTTTT GAAGGAACTA       960

TACAACGCAC ACATAGGCCA TCTTATGAAG ATAGAGTTTG TTTTGTAGCT ACTGTCAGGT      1020

TAGCTACACC TCAGTTCATC AAGGAAATGT GCACTGTTGA AGAACCCAAT GAAGAGTTTA      1080

CATCTAGACA TAGTTTAGAA TGGAAGTTTC TGTTTCTAGA TCACAGGGCA CCACCCATAA      1140

TAGGGTATTT GCCATTTGAA GTTCTGGGAA CATCAGGCTA TGATTACTAT CATGTGGATG      1200

ACCTAGAAAA TTTGGCAAAA TGTCATGAGC ACTTAATGCA ATATGGGAAA GGCAAATCAT      1260

GTTATTATAG GTTCCTGACT AAGGGGCAAC AGTGGATTTG GCTTCAGACT CATTATTATA      1320

TCACTTACCA TCAGTGGAAT TCAAGGCCAG AGTTTATTGT TTGTACTCAC ACTGTAGTAA      1380

GTTATGCAGA AGTTAGGGCT GAAAGACGAC GAGAACTTGG CATTGAAGAG TCTCTTCCTG      1440

AGACAGCTGC TGACAAAAGC CAAGATTCTG GGTCAGATAA TCGTATAAAC ACAGTCAGTC      1500

TCAAGGAAGC ATTGGAAAGG TTTGATCACA GCCCAACCCC TTCTGCCTCT TCTCGGAGTT      1560

CAAGAAAATC ATCTCACACG GCCGTCTCAG ACCCTTCCTC AACACCAACC AAGATCCCGA      1620

CGGATACGAG CACTCCACCC AGGCAGCATT TACCAGCTCA TGAGAAGATG GTGCAAAGAA      1680

GGTCATCATT TAGTAGTCAG TCCATAAATT CCCAGTCTGT TGGTTCATCA TTAACACAGC      1740

CAGTGATGTC TCAAGCTACA AATTTACCAA TTCCACAAGG CATGTCCCAG TTTCAGTTTT      1800

CAGCTCAATT AGGAGCCATG CAACATCTGA AAGACCAATT GGAACAACGG ACACGCATGA      1860

TAGAAGCAAA TATTCATCGG CAACAAGAAG AACTAAGAAA AATTCAAGAA CAACTTCAGA      1920

TGGTCCATGG TCAGGGGCTG CAGATGTTTT TGCAACAATC AAATCCTGGG TTGAATTTTG      1980

GTTCCGTTCA ACTTTCTTCT GGAAATTCAT CTAACATCCA GCAACTTGCA CCTATAAATA      2040

TGCAAGGCCA AGTTGTTCCT ACTAACCAGA TTCAAAGTGG AATGAATACT GGACACATTG      2100
```

```
GCACAACTCA GCACATGATA CAACAACAGA CTTTACAGAG TACATCAACT CAGAGTCAAC    2160

AAAATGTACT GAGTGGGCAC AGTCAGCAAA CATCTCTACC CAGTCAGACA CAGAGCACTC    2220

TTACAGCCCC ACTGTATAAC ACTATGGTGA TTTCTCAGCC TGCAGCCGGA AGCATGGTCC    2280

AGATTCCATC TAGTATGCCA CAAAACAGCA CCCAGAGTGC TGCAGTAACT ACATTCACTC    2340

AGGACAGGCA GATAAGATTT TCTCAAGGTC AACAACTTGT GACCAAATTA GTGACTGCTC    2400

CTGTAGCTTG TGGGGCAGTC ATGGTACCTA GTACTATGCT TATGGGCCAG GTGGTGACTG    2460

CATATCCTAC TTTTGCTACA CAACAGCAAC AGTCACAGAC ATTGTCAGTA ACGCAGCAGC    2520

AGCAGCAGCA GAGCTCCCAG GAGCAGCAGC TCACTTCAGT TCAGCAACCA TCTCAGGCTC    2580

AGCTGACCCA GCCACCGCAA CAATTTTTAC AGACTTCTAG GTTGCTCCAT GGGAATCCCT    2640

CAACTCAACT CATTCTCTCT GCTGCATTTC CTCTACAACA GAGCACCTTC CCTCAGTCAC    2700

ATCACCAGCA ACATCAGTCT CAGCAACAGC AGCAACTCAG CCGGCACAGG ACTGACAGCT    2760

TGCCCGACCC TTCCAAGGTT CAACCACAGT AGCACACGTG CTTCCTCTCT TGACATCAAG    2820

GGAGGAAGGG GATGGCCCAT TAAGAGTTAC TCAGATGACC TGAGGAAAGG AGGGAAAGTT    2880

CCAGCAGTTT CATGAGATGC AGTATTGAGT GTTCTAGTTC CTGGAATTAG TTGGCAGAGA    2940

AAATGCTGCC TAGTGCTACA GATGTACATT AAATACCAGC CAGCAGGAGG TGATCATAGG    3000

GGCACAGCCA GTTCTGACAG TGTTTTAGGT GCCTGGATAT TTTTTGATGG AAAAAGAATA    3060

TATTGCCAAA TATTAAGAAG CTCAGCTATG AAATGACCTC CAGGGAATCA GAAAGGCACT    3120

AATGATGTTA GTAACTTTTA GTGGTTCTGT GCCTCTTATC AAGTGTTACA GAGGACATAC    3180

CACTGCCATG TCAGGGGTTT GCTTACAGTG ATGCCATGAA GACAGTCCAG TAGACTTGGT    3240

AGCGACCCCC TCCCCCAACC CCTCTCCCTT TTCAGATAAT GATGGAACAG TAATTACTTT    3300

CAGAATGTTG TGTGGGTTCA AATTCTCTAT GTACAGATGA TGTAAAAATA TGTATATGTC    3360

TAGATAAAAG GAGAGAAAGC AAAACATTTT GTATGCTGCA TGAAAGCGTT ATCTCTTCCT    3420

TACAGGTGTG AGCACCTTTC CTGAAATTCT GACACCATGT GCAAACTGAT CCATCCTGTT    3480

TTTCCTTTTG TTTACAACAC AGTAGTGTTC TGTTCACTTT TCCGGGCAC AAGTTTTTTT     3540

GTTCATACTT TGGCTGTGAT GTCACAGTTT GTTCAGTGAG GTATGATGTG CTGCTGGGAA    3600

TGGATTTTTT TTTTTCAGGT TAAATTATTG ATACAACAGG ATTTTCAAGT TATTCAGAAA    3660

TATCCCTCAT TTCATTATTT TTCAATTATG TTTGAAAATA GGATTTGCAC TGCTTTATTT    3720

TAGGTGGCTG GGAGTTTTGA TTGCATATTT TGTTATAGTT CATAGTTGGA AATATTTGCG    3780

TAAATGGTTT TCAACAAGCC TGAAAGTAAT TTCAAGAATG TTTCAGTTAT AGAGGTAAAA    3840

TTTGCACACA AAACATCTTA GGCACTTTTT AACATTCTCA ATCATGGGAA TTTTAACTTT    3900

TGGGATTTGT TGAAATCTTT TTTATTATCC TTCACAATTT CAATGCTTCT TTTAGTCAGA    3960

AATGATTCAG GGTTATTTGA GGGGAAAAAA CCCCATAGTG CCTTGATTTT AATTCAGGTG    4020

ATAACTCACC ATCTTGAAGT CATTGTCCGG TTTCCGTAGC AGTTTTGAAA CCTTAGTACC    4080

TTTTTAACAG CATGTGGGTG TCAGTGTCAT TATTAGTCTC CTAATAAGTT CCTCTGAAGA    4140

CTGCTATCAG TCTCTTGGAC TGGAGTTACA AATAATTTAG AAATAAAAGA TGATAACCTA    4200

ACACTATCAT AGTTATTAAT GTGATCCTAA AATTGTTTCC TAAATCAGCA TTTTTCTTTA    4260

GTCATTTAAG AATTTACCAG AAATATTTGC TCAATATGAT CTTGATATTC CTACAAAGAA    4320

AAAAGAAGGG GTAGGGATTT GGCTATGCCT TCACTACAAC ATTAGAATAT TGTAACTCAC    4380

ATGCCTTCTA AACGTGAACT AAGATTTCCT TTGGCAATAT CATATTCTAA AAGTAATAAA    4440
```

```
TTCCAATACA AGTTACATAC ATTTAAAAAA CATTTTACAG ATTTTATGGT ACTAATGAAA    4500

TTTACAGTGA TAGAACAAAA GAGGATTAGT AGAAAATACA TTATTAGAAT ATAAAAAATG    4560

TTATTACTGA GGAAAGGGAG GAGAGGACAA GTGTAATAAA TCAAAATTGA CCTCAAAAGA    4620

AAATGTGTAA CAGAGTTGAG GTTGTTAAAA CAGAAAAGGT TCTGAATAAT GAAGATTAAC    4680

CTAATGCAGA ATTGCTAGGT AAAGAGGTCA GGGGAATGCT AAGCCAGTTC TTAAGACTTC    4740

TCTGTCCTCT GCTTTGCTGT TATCCTTAAG GCATATACTT TGTCTTTCTG CAGAAAATTC    4800

TACCTGGCTA CAATTACTTT GAACATTAAT GTTGAAAAAG AAAACAACCA AGAAAATTG    4860

GTACTTACCC TTCTACAAAA GAAGTGTGAC TAGATATCAA TCAGTAATTA ACATATCAAG    4920

GAGCTCTTCT AGCTAAATGA CCATCCAGTA GAGATTTCCC ACATTCCCAT GAATATCAAG    4980

AATAGTTGTC AGAATATGTA TGTACCTGAG CATATGTACA CAGACAAGGG GGATGTTGTG    5040

GAATATGGCA ATAGCATTGT TCTTCTCCCC TTTCAAATTG CCTTTCTTGA CCTTATGCCA    5100

TTCCATATAT ATCTGAGTTG TGCCTCATTT ATTTATTGGC AATACCTAGT GATACGGATT    5160

TAGCTAACAA AAGATATGAA GAACTATTAT ATTGAGGCCT GTCCTCTACA TACCACACTT    5220

AAAAGATGGT GAACTGTGAG TACTACTTAG GTTGACAGCA ACAAAGCATA AGACAAGCCC    5280

CAGGTAAACG TCTAAACTGT TTACTCACAT TGTCCTACTC CAGCCCCTTC AATTATTTCC    5340

CATCTCCACA AATAGTCGGG GGAAAAAATT AAAATTTTCC TTTATGATTC TTACTGTTCT    5400

TCGCAGCTCA TCTTTTCCTG CTTAGAATTA ACCATTGCTA ATTTAAAGGA GCAGCTAGCT    5460

GCTTTTCTGT CAGTCTGAAG CGTAGTAGTG GAAGAGGTAG TAAGCACCAG CTGCCTCTTT    5520

GCTGCTTTGT TTTCCTCCTG ATTCTCTTAA ATTTGGGTTG CAAAGCTATC CCGCCCCCCA    5580

CCCTGCCCCA TGAAACTTGA GCATTCAAAT GAAGATTCAG CAGTGTCTGT TCTTCATTTC    5640

TATAGCCAAA GCTGTTAGTT AAAATCCCAA ATCTATAGCA TTTAAAGATA CCAAATAGAA    5700

ACACCTTCCA GCTTT                                                    5715
```

(2) INFORMATION FOR SEQ ID NO:2:

(i) SEQUENCE CHARACTERISTICS:
        (A) LENGTH: 846 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Leu Phe Thr Val Ser Cys Ser Lys Met Ser Ser Ile Val Asp Arg
 1               5                  10                  15

Asp Asp Ser Ser Ile Phe Asp Gly Leu Val Glu Asp Asp Lys Asp
            20                  25                  30

Lys Ala Lys Arg Val Ser Arg Asn Lys Ser Glu Lys Lys Arg Arg Asp
        35                  40                  45

Gln Phe Asn Val Leu Ile Lys Glu Leu Gly Ser Met Leu Pro Gly Asn
    50                  55                  60

Ala Arg Lys Met Asp Lys Ser Thr Val Leu Gln Lys Ser Ile Asp Phe
65                  70                  75                  80

Leu Arg Lys His Lys Glu Ile Thr Ala Gln Ser Asp Ala Ser Glu Ile
                85                  90                  95

Arg Gln Asp Trp Lys Pro Thr Phe Leu Ser Asn Glu Glu Phe Thr Gln
            100                 105                 110

Leu Met Leu Glu Ala Leu Asp Gly Phe Phe Leu Ala Ile Met Thr Asp
```

-continued

```
                115                 120                 125
Gly Ser Ile Ile Tyr Val Ser Glu Ser Val Thr Ser Leu Leu Glu His
        130                 135                 140

Leu Pro Ser Asp Leu Val Asp Gln Ser Ile Phe Asn Phe Ile Pro Glu
145                 150                 155                 160

Gly Glu His Ser Glu Val Tyr Lys Ile Leu Ser Thr His Leu Leu Glu
                165                 170                 175

Ser Asp Ser Leu Thr Pro Glu Tyr Leu Lys Ser Lys Asn Gln Leu Glu
            180                 185                 190

Phe Cys Cys His Met Leu Arg Gly Thr Ile Asp Pro Lys Glu Pro Ser
        195                 200                 205

Thr Tyr Glu Tyr Val Lys Phe Ile Gly Asn Phe Lys Ser Leu Asn Ser
    210                 215                 220

Val Ser Ser Ala His Asn Gly Phe Glu Gly Thr Ile Gln Arg Thr
225                 230                 235                 240

His Arg Pro Ser Tyr Glu Asp Arg Val Cys Phe Val Ala Thr Val Arg
                245                 250                 255

Leu Ala Thr Pro Gln Phe Ile Lys Glu Met Cys Thr Val Glu Glu Pro
            260                 265                 270

Asn Glu Glu Phe Thr Ser Arg His Ser Leu Glu Trp Lys Phe Leu Phe
        275                 280                 285

Leu Asp His Arg Ala Pro Pro Ile Ile Gly Tyr Leu Pro Phe Glu Val
290                 295                 300

Leu Gly Thr Ser Gly Tyr Asp Tyr Tyr His Val Asp Asp Leu Glu Asn
305                 310                 315                 320

Leu Ala Lys Cys His Glu His Leu Met Gln Tyr Gly Lys Gly Lys Ser
                325                 330                 335

Cys Tyr Tyr Arg Phe Leu Thr Lys Gly Gln Gln Trp Ile Trp Leu Gln
            340                 345                 350

Thr His Tyr Tyr Ile Thr Tyr His Gln Trp Asn Ser Arg Pro Glu Phe
        355                 360                 365

Ile Val Cys Thr His Thr Val Ser Tyr Ala Glu Val Arg Ala Glu
    370                 375                 380

Arg Arg Arg Glu Leu Gly Ile Glu Glu Ser Leu Pro Glu Thr Ala Ala
385                 390                 395                 400

Asp Lys Ser Gln Asp Ser Gly Ser Asp Asn Arg Ile Asn Thr Val Ser
                405                 410                 415

Leu Lys Glu Ala Leu Glu Arg Phe Asp His Ser Pro Thr Pro Ser Ala
            420                 425                 430

Ser Ser Arg Ser Ser Arg Lys Ser Ser His Thr Ala Val Ser Asp Pro
        435                 440                 445

Ser Ser Thr Pro Thr Lys Ile Pro Thr Asp Thr Ser Thr Pro Pro Arg
450                 455                 460

Gln His Leu Pro Ala His Glu Lys Met Val Gln Arg Arg Ser Ser Phe
465                 470                 475                 480

Ser Ser Gln Ser Ile Asn Ser Gln Ser Val Gly Ser Ser Leu Thr Gln
                485                 490                 495

Pro Val Met Ser Gln Ala Thr Asn Leu Pro Ile Pro Gln Gly Met Ser
            500                 505                 510

Gln Phe Gln Phe Ser Ala Gln Leu Gly Ala Met Gln His Leu Lys Asp
        515                 520                 525

Gln Leu Glu Gln Arg Thr Arg Met Ile Glu Ala Asn Ile His Arg Gln
530                 535                 540
```

-continued

```
Gln Glu Glu Leu Arg Lys Ile Gln Glu Gln Leu Gln Met Val His Gly
545                 550                 555                 560

Gln Gly Leu Gln Met Phe Leu Gln Gln Ser Asn Pro Gly Leu Asn Phe
                565                 570                 575

Gly Ser Val Gln Leu Ser Ser Gly Asn Ser Ser Asn Ile Gln Gln Leu
                580                 585                 590

Ala Pro Ile Asn Met Gln Gly Gln Val Val Pro Thr Asn Gln Ile Gln
                595                 600                 605

Ser Gly Met Asn Thr Gly His Ile Gly Thr Thr Gln His Met Ile Gln
            610                 615                 620

Gln Gln Thr Leu Gln Ser Thr Ser Thr Gln Ser Gln Gln Asn Val Leu
625                 630                 635                 640

Ser Gly His Ser Gln Gln Thr Ser Leu Pro Ser Gln Thr Gln Ser Thr
                645                 650                 655

Leu Thr Ala Pro Leu Tyr Asn Thr Met Val Ile Ser Gln Pro Ala Ala
                660                 665                 670

Gly Ser Met Val Gln Ile Pro Ser Ser Met Pro Gln Asn Ser Thr Gln
            675                 680                 685

Ser Ala Ala Val Thr Thr Phe Thr Gln Asp Arg Gln Ile Arg Phe Ser
            690                 695                 700

Gln Gly Gln Gln Leu Val Thr Lys Leu Val Thr Ala Pro Val Ala Cys
705                 710                 715                 720

Gly Ala Val Met Val Pro Ser Thr Met Leu Met Gly Gln Val Val Thr
                725                 730                 735

Ala Tyr Pro Thr Phe Ala Thr Gln Gln Gln Gln Ser Gln Thr Leu Ser
                740                 745                 750

Val Thr Gln Gln Gln Gln Gln Ser Ser Gln Glu Gln Gln Leu Thr
            755                 760                 765

Ser Val Gln Gln Pro Ser Gln Ala Gln Leu Thr Gln Pro Pro Gln Gln
            770                 775                 780

Phe Leu Gln Thr Ser Arg Leu Leu His Gly Asn Pro Ser Thr Gln Leu
785                 790                 795                 800

Ile Leu Ser Ala Ala Phe Pro Leu Gln Gln Ser Thr Phe Pro Gln Ser
                805                 810                 815

His His Gln Gln His Gln Ser Gln Gln Gln Gln Leu Ser Arg His
            820                 825                 830

Arg Thr Asp Ser Leu Pro Asp Pro Ser Lys Val Gln Pro Gln
            835                 840                 845
```

EXPRESSION SYSTEM FOR HSCLOCK

FIELD OF INVENTION

This invention relates to new uses for polynucleotides and polypeptides encoded by them and to their production. More particularly, the polynucleotides and polypeptides of the present invention relate to the clock gene family, hereinafter referred to as HSCLOCK. The invention also relates to inhibiting or activating the action of such polynucleotides and polypeptides.

BACKGROUND OF THE INVENTION

Circadian rhythmicity represents a complex behavioural and physiological phenotype. Clock genes have been identified in non-mammalian organisms, most notably, the period (per) and timeless (tim) genes in Drosophila and the frequency (frq) gene in Neurospora (reviewed in J. C. Hall, Trends Neurosci., 18: 230–240, 1995; J. C. Dunlap, Ann.Rev.Genet., 30: 579–601, 1996). A mouse clock gene has recently been identified by positional cloning (D. P. King et al., Cell, 89: 641–653, 1997). Mutation and transgenic studies (M. P. Antoch et al., Cell, 89: 655–667, 1997) confirm the involvement of the clock gene in circadian rhythmicity. The mouse clock protein contains both a DNA binding domain and a protein dimerisation domain indicating that it could, in combination with other proteins, regulate circadian rhythmicity by regulating gene transcription. The pattern of mouse clock gene expresssion is consistent with its role in circadian rhythms with highest levels of expression in the hypothalamus and eye, both of which are known to contain self-sustaining circadian oscillators. The mouse clock gene is also expressed in many tissues throughout the body. Similarly the drosophila gene has a wide tissue distribution pattern.

Recently Nagase, T. et al (DNA Res. 4, 141–150, 1997) published a set of full-length, but unidentified cDNAs expressed in human brain. The present invention identifies one of these cDNA sequences as encoding a human clock gene. The gene from which this human clock cDNA has been derived has been mapped to chromosome 4 (Nagase, T. et al (DNA Res. 4, 141–150, 1997). It has been predicted independently that the human clock gene maps to 4q12–4q13 by synteny with the mouse clock locus (King, D P et al Genetics 146, 1049–1060, 1997).

SUMMARY OF THE INVENTION

In one aspect, the invention relates to the use of HSCLOCK polynucleotides and polypeptides. Such uses include the treatment of sleep disorders, jet lag, pathologies that occur in advanced age, among others. In a further aspect the invention relates to HSCLOCK recombinant materials and methods for their production. Another aspect of the invention relates to methods for using such recombinant HSCLOCK polypeptides and polynucleotides. In still another aspect, the invention relates to methods to identify agonists and antagonists using the materials provided by the invention, and treating conditions associated with HSCLOCK imbalance with the identified compounds. Yet another aspect of the invention relates to diagnostic assays for detecting diseases associated with inappropriate HSCLOCK activity or levels.

DESCRIPTION OF THE INVENTION

Definitions

The following definitions are provided to facilitate understanding of certain terms used frequently herein.

"HSCLOCK" refers, among others, generally to a polypeptide having the amino acid sequence set forth in SEQ ID NO:2 or an allelic variant thereof.

"HSCLOCK activity or HSCLOCK polypeptide activity" or "biological activity of the HSCLOCK or HSCLOCK polypeptide" refers to the metabolic or physiologic function of said HSCLOCK including similar activities or improved activities or these activities with decreased undesirable side-effects. Also included are antigenic and immunogenic activities of said HSCLOCK.

"HSCLOCK gene" refers to a polynucleotide having the nucleotide sequence set forth in SEQ ID NO:1 or allelic variants thereof and/or their complements.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Polynucleotide" generally refers to any polyribonucleotide or polydeoxribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, PROTEINS—STRUCTURE AND MOLECULAR PROPERTIES, 2nd Ed., T. E. Creighton, W. H. Freeman and Company, New York, 1993 and Wold, F., Post-translational Protein Modifications: Perspectives and Prospects, pgs. 1–12 in POSTTRANSLATIONAL COVALENT MODIFICATION OF PROTEINS, B. C. Johnson, Ed., Academic Press, New York, 1983; Seifter et al., "Analysis for protein modifications and nonprotein cofactors", Meth Enzymol (1990) 182:626–646 and Rattan et al., "Protein Synthesis: Posttranslational Modifications and Aging", Ann NY Acad Sci (1992) 663:48–62.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Percent identity", as known in the art, is a measure of the relationship between two polypeptide sequences or two polynucleotide sequences, as determined by comparing their sequences. In general, the two sequences to be compared are aligned to give a maximum correlation between the sequences. The alignment of the two sequences is examined and the number of positions giving an exact amino acid or nucleotide correspondence between the two sequences determined, divided by the total length of the alignment and multiplied by 100 to give a % identity figure. This % identity figure may be determined over the whole length of the sequences to be compared, which is particularly suitable for sequences of the same or very similar length and which are highly homologous, or over shorter defined lengths, which is more suitable for sequences of unequal length or which have a lower level of homology.

"Percent similarity", as known in the art, is a further measure of the relationship between two polypeptide sequences. The two sequences being compared are aligned to give maximum correlation between the sequences. The alignment of the two sequences is examined at each position and a score is determined according to the chemical and/or physical properties of the amino acids being compared at that position. Such chemical and/or physical properties include charge, size and hydrophobicity of the amino acid side chains.

Methods for comparing the identity and similarity of two or more sequences are well known in the art. Thus for instance, programs available in the Wisconsin Sequence Analysis Package, version 9.1 (Devereux J et al, Nucleic Acids Res, 12, 387–395, 1984, available from Genetics Computer Group, Madison, Wis., USA), for example the programs BESTFIT and GAP, may be used to determine the % identity between two polynucleotides and the % identity and the % similarity between two polypeptide sequences. BESTFIT uses the "local homology" algorithm of Smith and Waterman (Advances in Applied Mathematics, 2, 482–489, 1981) and finds the best single region of similarity between two sequences. BESTFIT is more suited to comparing two polynucleotide or two polypeptide sequences which are dissimilar in length, the program assuming that the shorter sequence represents a portion of the longer. In comparison, GAP aligns two sequences, finding a "maximum similarity", according to the algorithm of Neddleman and Wunsch (J Mol Biol, 48, 443–453, 1970). GAP is more suited to comparing sequences which are approximately the same length and an alignment is expected over the entire length. Preferably, the parameters "Gap Weight" and "Length Weight" used in each program are 50 and 3, for polynucleotide sequences and 12 and 4 for polypeptide sequences, respectively. Preferably, % identities and similarities are determined when the two sequences being compared are optimally aligned.

Other programs for determining identity and/or similarity between sequences are also known in the art, for instance the BLAST family of programs (Altschul S F et al, J Mol Biol, 215, 403–410, 1990, Altschul S F et al, Nucleic Acids Res., 25:389–3402, 1997, available from the National Center for Biotechnology Information (NCBI), Bethesda, Md., USA and accessible through the home page of the NCBI at www.ncbi.nlm.nih.gov) and FASTA (Pearson W R and Lipman D J, Proc Nat Acad Sci USA, 85, 2444–2448,1988, available as part of the Wisconsin Sequence Analysis Package). Preferably, the BLOSUM62 amino acid substitution matrix (Henikoff S and Henikoff J G, Proc. Nat. Acad Sci. USA, 89, 10915–10919, 1992) is used in polypeptide sequence comparisons including where nucleotide sequences are first translated into amino acid sequences before comparison.

Preferably, the program BESTFIT is used to determine the % identity of a query polynucleotide or a polypeptide sequence with respect to a polynucleotide or a polypeptide sequence of the present invention, the query and the reference sequence being optimally aligned and the parameters of the program set at the default value.

POLYPEPTIDES OF THE INVENTION

In one aspect, the present invention relates to HSCLOCK polypeptides (or HSCLOCK proteins). The HSCLOCK polypeptides include the polypeptide of SEQ ID NO:2; as well as polypeptides comprising the amino acid sequence of SEQ ID NO: 2; and polypeptides comprising an amino acid sequence which has at least 80% identity to that of SEQ ID NO:2 over its entire length, and still more preferably at least 90% identity, and even still more preferably at least 95% identity to SEQ ID NO: 2. Furthermore, those amino acid sequences with at least 97–99% are highly preferred. Also included within HSCLOCK polypeptides are polypeptides having an amino acid sequence which has at least 80% identity to the polypeptide sequence of SEQ ID NO:2 over its entire length, and still more preferably at least 90% identity, and still more preferably at least 95% identity to SEQ ID NO:2. Furthermore, those with at least 97–99% are highly preferred. Preferably HSCLOCK polypeptide exhibit at least one biological activity of HSCLOCK.

The HSCLOCK polypeptides may be in the form of the "mature" protein or may be a part of a larger protein such as a fusion protein. It is often advantageous to include an additional amino acid sequence which contains secretory or leader sequences, pro-sequences, sequences which aid in purification such as multiple histidine residues, or an additional sequence for stability during recombinant production.

Fragments of the HSCLOCK polypeptides are also included in the invention. A fragment is a polypeptide having an amino acid sequence that entirely is the same as part, but not all, of the amino acid sequence of the aforementioned HSCLOCK polypeptides. As with HSCLOCK polypeptides, fragments may be "free-standing," or comprised within a larger polypeptide of which they form a part or region, most preferably as a single continuous region. Representative examples of polypeptide fragments of the invention, include, for example, fragments from about amino acid number 1–20, 21–40, 41–60, 61–80, 81–100, and 101 to the end of HSCLOCK polypeptide. In this context "about" includes the particularly recited ranges larger or smaller by several, 5, 4, 3, 2 or 1 amino acid at either extreme or at both extremes.

Preferred fragments include, for example, truncation polypeptides having the amino acid sequence of HSCLOCK polypeptides, except for deletion of a continuous series of residues that includes the amino terminus, or a continuous series of residues that includes the carboxyl terminus or deletion of two continuous series of residues, one including the amino terminus and one including the carboxyl terminus. Also preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Other preferred fragments are biologically active fragments. Biologically active fragments are those that mediate HSCLOCK activity, including those with a similar activity or an improved activity, or with a decreased undesirable activity. Also included are those that are antigenic or immunogenic in an animal, especially in a human.

Preferably, all of these polypeptide fragments retain the biological activity of the HSCLOCK, including antigenic activity. Variants of the defined sequence and fragments also form part of the present invention. Preferred variants are those that vary from the referents by conservative amino acid substitutions—i.e., those that substitute a residue with another of like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are variants in which several, 5–10, 1–5, or 1–2 amino acids are substituted, deleted, or added in any combination.

The HSCLOCK polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

POLYNUCLEOTIDES OF THE INVENTION

Another aspect of the invention relates to HSCLOCK polynucleotides. HSCLOCK polynucleotides include isolated polynucleotides which encode the HSCLOCK polypeptides and fragments, and polynucleotides closely related thereto. More specifically, HSCLOCK polynucleotides of the invention include a polynucleotide comprising the nucleotide sequence contained in SEQ ID NO:1 encoding a HSCLOCK polypeptide of SEQ ID NO: 2, and a polynucleotide having the particular sequence of SEQ ID NO:1. HSCLOCK polynucleotides further include a polynucleotide comprising a nucleotide sequence that has at least 80% identity over its entire length to a nucleotide sequence encoding the HSCLOCK polypeptide of SEQ ID NO:2, and a polynucleotide comprising a nucleotide sequence that is at least 80% identical to of SEQ ID NO:1 over its entire length. In this regard, polynucleotides at least 90% identical are particularly preferred, and those with at least 95% are especially preferred. Furthermore, those with at least 97% identity are highly preferred and those with at least 98–99% are most highly preferred, polynucleotides with at least 99% being the most preferred. Also included under HSCLOCK polynucleotides is a nucleotide sequence which has sufficient identity to a nucleotide sequence contained in SEQ ID NO:1 to hybridize under conditions useable for amplification or for use as a probe or marker. The invention also provides polynucleotides which are complementary to such HSCLOCK polynucleotides.

HSCLOCK of the invention is structurally related to other proteins of the clock gene family. The cDNA sequence of SEQ ID NO:1 contains an open reading frame (nucleotide number 252 to 2789) encoding a polypeptide of 846 amino acids of SEQ ID NO:2. Amino acid sequence of SEQ ID NO:2 has about 96% identity (using Smith-Waterman) in 846 amino acid residues with mouse clock protein (D. P. King et al., Cell 89: 641–653, 1997). The nucleotide sequence of SEQ ID NO:1 has about 87% identity (using Smith-Waterman) in 4663 nucleotide residues with the cDNA encoding the mouse clock protein (D. P. King et al., Cell 89: 641–653, 1997).

An HSCLOCK polynucleotide may be obtained using standard cloning and screening, from a cDNA library derived from mRNA in cells of human brain using the expressed sequence tag (EST) analysis (Adams, M. D., et al. *Science* (1991) 252:1651–1656; Adams, M. D. et al., *Nature*, (1992) 355:632–634; Adams, M. D., et al., *Nature* (1995) 377 Supp:3–174). Polynucleotides of the invention can also be obtained from natural sources such as genomic DNA libraries or can be synthesized using well known and commercially available techniques.

The nucleotide sequence encoding HSCLOCK polypeptide of SEQ ID NO:2 may be identical to the polypeptide encoding sequence contained in SEQ ID NO:1 (nucleotide number 252 to 2789), or it may be a sequence, which as a result of the redundancy (degeneracy) of the genetic code, also encodes the polypeptide of SEQ ID NO:2.

When the polynucleotides of the invention are used for the recombinant production of HSCLOCK polypeptide, the polynucleotide may include the coding sequence for the mature polypeptide or a fragment thereof, by itself, the coding sequence for the mature polypeptide or fragment in reading frame with other coding sequences, such as those encoding a leader or secretory sequence, a pre-, or pro- or prepro- protein sequence, or other fusion peptide portions. For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., *Proc Natl Acad Sci USA* (1989) 86:821–824, or is an HA tag. The polynucleotide may also contain non-coding 5' and 3' sequences, such as transcribed, non-translated sequences, splicing and polyadenylation signals, ribosome binding sites and sequences that stabilize mRNA.

Further preferred embodiments are polynucleotides encoding HSCLOCK variants comprise the amino acid sequence HSCLOCK polypeptide of SEQ ID NO:2 in which several, 5–10, 1–5, 1–3, 1–2 or 1 amino acid residues are substituted, deleted or added, in any combination.

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 80%, and preferably at least 90%, and more preferably at least 95%, yet even more preferably 97–99% identity between the sequences.

Polynucleotides of the invention, which are identical or sufficiently identical to a nucleotide sequence contained in SEQ ID NO:1 or a fragment thereof, may be used as hybridization probes for cDNA and genomic DNA, to isolate full-length cDNAs and genomic clones encoding HSCLOCK polypeptide and to isolate cDNA and genomic clones of other genes (including genes encoding homologs and orthologs from species other than human) that have a high sequence similarity to the HSCLOCK gene. Such hybridization techniques are known to those of skill in the art. Typically these nucleotide sequences are 80% identical, preferably 90% identical, more preferably 95% identical to that of the referent. The probes generally will comprise at least 15 nucleotides. Preferably, such probes will have at least 30 nucleotides and may have at least 50 nucleotides. Particularly preferred probes will range between 30 and 50 nucleotides.

In one embodiment, to obtain a polynucleotide encoding HSCLOCK polypeptide, including homologs and orthologs from species other than human, comprises the steps of screening an appropriate library under stringent hybridization conditions with a labeled probe having the SEQ ID NO:1 or a fragment thereof; and isolating full-length cDNA and genomic clones containing said polynucleotide sequence. Thus in another aspect, HSCLOCK polynucleotides of the present invention further include a nucleotide sequence comprising a nucleotide sequence that hybridize under stringent condition to a nucleotide sequence having SEQ ID NO: 1 or a fragment thereof. Also included with HSCLOCK polypeptides are polypeptide comprising amino acid sequence encoded by nucleotide sequence obtained by the above hybridization condition. Such hybridization techniques are well known to those of skill in the art. Stringent hybridization conditions are as defined above or, alternatively, conditions under overnight incubation at 42° C. in a solution comprising: 50% formamide, 5×SSC (150 mM NaCl, 15 mM trisodium citrate), 50 mM sodium phosphate pH7.6), 5×Denhardt's solution, 10% dextran sulfate, and 20 microgram/ml denatured, sheared salmon sperm DNA, followed by washing the filters in 0.1×SSC at about 65° C.

The polynucleotides and polypeptides of the present invention may be employed as research reagents and materials for discovery of treatments and diagnostics to animal and human disease.

VECTORS, HOST CELLS, EXPRESSION

The present invention also relates to vectors which comprise a polynucleotide or polynucleotides of the present invention, and host cells which are genetically engineered with vectors of the invention and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al., *BASIC METHODS IN MOLECULAR BIOLOGY* (1986) and Sambrook et al., *MOLECULAR CLONING: A LABORATORY MANUAL,* 2nd Ed., Cold Spring Harbor Laboratory Press, Cold Spring Harbor, N.Y. (1989) such as calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as streptococci, staphylococci, *E. coli,* Streptomyces and *Bacillus subtilis* cells; fungal cells, such as yeast cells and Aspergillus cells; insect cells such as Drosophila S2 and Spodoptera Sf9 cells; animal cells such as CHO, COS, HeLa, C127, 3T3, BHK, HEK 293 and Bowes melanoma cells; and plant cells.

A great variety of expression systems can be used. Such systems include, among others, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al., *MOLECULAR CLONING, A LABORATORY MANUAL* (supra).

For secretion of the translated protein into the lumen of the endoplasmic reticulum, into the periplasmic space or into the extracellular environment, appropriate secretion signals may be incorporated into the desired polypeptide. These signals may be endogenous to the polypeptide or they may be heterologous signals.

If the HSCLOCK polypeptide is to be expressed for use in screening assays, generally, it is preferred that the polypeptide be produced at the surface of the cell. In this event, the cells may be harvested prior to use in the screening assay. If HSCLOCK polypeptide is secreted into the medium, the medium can be recovered in order to recover and purify the polypeptide; if produced intracellularly, the cells must first be lysed before the polypeptide is recovered. HSCLOCK polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during isolation and or purification.

DIAGNOSTIC ASSAYS

This invention also relates to the use of HSCLOCK polynucleotides for use as diagnostic reagents. Detection of a mutated form of HSCLOCK gene associated with a dysfunction will provide a diagnostic tool that can add to or define a diagnosis of a disease or susceptibility to a disease which results from under-expression, over-expression or altered expression of HSCLOCK. Individuals carrying mutations in the HSCLOCK gene may be detected at the DNA level by a variety of techniques.

Nucleic acids for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled HSCLOCK nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing. See, e.g., Myers et al., *Science* (1985) 230:1242. Sequence changes at specific locations may also be revealed by nuclease protection assays, such as RNase and S1 protection or the chemical cleavage method. See Cotton et al., *Proc Natl Acad Sci USA* (1985) 85: 4397–4401. In another embodiment, an array of oligonucleotides probes comprising HSCLOCK nucleotide sequence or fragments thereof can be constructed to conduct efficient screening of e.g., genetic mutations. Array technology methods are well known and have general applicability and can be used to address a variety of questions in molecular genetics including gene expression, genetic linkage, and genetic variability. (See for example: M. Chee et al., Science, Vol 274, pp 610–613 (1996)).

The diagnostic assays offer a process for diagnosing or determining a susceptibility to sleep disorders, jet lag, pathologies that occur in advanced age through detection of mutation in the HSCLOCK gene by the methods described.

In addition, sleep disorders, jet lag, pathologies that occur in advanced age, can be diagnosed by methods comprising determining from a sample derived from a subject an abnormally decreased or increased level of HSCLOCK polypeptide or HSCLOCK mRNA. Decreased or increased expression can be measured at the RNA level using any of the methods well known in the art for the quantitation of polynucleotides, such as, for example, PCR, RT-PCR, RNase protection, Northern blotting and other hybridization methods. Assay techniques that can be used to determine levels of a protein, such as an HSCLOCK polypeptide, in a sample derived from a host are well-known to those of skill in the art. Such assay methods include radioimmunoassays, competitive-binding assays, Western Blot analysis and ELISA assays.

Thus in another aspect, the present invention relates to a diagonostic kit for a disease or suspectability to a disease, particularly sleep disorders, jet lag, pathologies that occur in advanced age, which comprises:
(a) a HSCLOCK polynucleotide, preferably the nucleotide sequence of SEQ ID NO: 1, or a fragment thereof;
(b) a nucleotide sequence complementary to that of (a);
(c) a HSCLOCK polypeptide, preferably the polypeptide of SEQ ID NO: 2, or a fragment thereof; or
(d) an antibody to a HSCLOCK polypeptide, preferably to the polypeptide of SEQ ID NO: 2.

It will be appreciated that in any such kit, (a), (b), (c) or (d) may comprise a substantial component.

ANTIBODIES

The polypeptides of the invention or their fragments or analogs thereof, or cells expressing them can also be used as immunogens to produce antibodies immunospecific for the HSCLOCK polypeptides. The term "immunospecific" means that the antibodies have substantially greater affinity for the polypeptides of the invention than their affinity for other related polypeptides in the prior art.

Antibodies generated against the HSCLOCK polypeptides can be obtained by administering the polypeptides or epitope-bearing fragments, analogs or cells to an animal, preferably a nonhuman, using routine protocols. For preparation of monoclonal antibodies, any technique which provides antibodies produced by continuous cell line cultures can be used. Examples include the hybridoma technique (Kohler, G. and Milstein, C., *Nature* (1975) 256:495–497), the trioma technique, the human B-cell hybridoma technique (Kozbor et al., *Immunology Today* (1983) 4:72) and the EBV-hybridoma technique (Cole et al., MONOCLONAL ANTIBODIES AND CANCER THERAPY, pp. 77–96, Alan R. Liss, Inc., 1985).

Techniques for the production of single chain antibodies (U.S. Pat. No. 4,946,778) can also be adapted to produce single chain antibodies to polypeptides of this invention. Also, transgenic mice, or other organisms including other mammals, may be used to express humanized antibodies.

The above-described antibodies may be employed to isolate or to identify clones expressing the polypeptide or to purify the polypeptides by affinity chromatography.

Antibodies against HSCLOCK polypeptides may also be employed to treat sleep disorders, jet lag, pathologies that occur in advanced age, among others.

VACCINES

Another aspect of the invention relates to a method for inducing an immunological response in a mammal which comprises inoculating the mammal with HSCLOCK polypeptide, or a fragment thereof, adequate to produce antibody and/or T cell immune response to protect said animal from sleep disorders, jet lag, pathologies that occur in advanced age, among others. Yet another aspect of the invention relates to a method of inducing immunological response in a mammal which comprises, delivering HSCLOCK polypeptide via a vector directing expression of HSCLOCK polynucleotide in vivo in order to induce such an immunological response to produce antibody to protect said animal from diseases.

Further aspect of the invention relates to an immunological/vaccine formulation (composition) which, when introduced into a mammalian host, induces an immunological response in that mammal to a HSCLOCK polypeptide wherein the composition comprises a HSCLOCK polypeptide or HSCLOCK gene. The vaccine formulation may further comprise a suitable carrier. Since HSCLOCK polypeptide may be broken down in the stomach, it is preferably administered parenterally (including subcutaneous, intramuscular, intravenous, intradermal etc. injection). Formulations suitable for parenteral administration include aqueous and non-aqueous sterile injection solutions which may contain anti-oxidants, buffers, bacteriostats and solutes which render the formulation isotonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

SCREENING ASSAYS

The HSCLOCK polypeptide of the present invention may be employed in a screening process for compounds which activate (agonists) or inhibit activation of (antagonists, or otherwise called inhibitors) the HSCLOCK polypeptide of the present invention. Thus, polypeptides of the invention may also be used to assess identify agonist or antagonists from, for example, cells, cell-free preparations, chemical libraries, and natural product mixtures. These agonists or antagonists may be natural or modified substrates, ligands, receptors, enzymes, etc., as the case may be, of the polypeptide of the present invention; or may be structural or functional mimetics of the polypeptide of the present invention. See Coligan et al., *Current Protocols in Immunology* 1(2) :Chapter 5 (1991). HSCLOCK polypeptides are responsible for many biological functions, including many pathologies. Accordingly, it is desirous to find compounds and drugs which stimulate HSCLOCK polypeptide on the one hand and which can inhibit the function of HSCLOCK polypeptide on the other hand. In general, agonists are employed for therapeutic and prophylactic purposes for such conditions as sleep disorders, jet lag, pathologies that occur in advanced age. Antagonists may be employed for a variety of therapeutic and prophylactic purposes for such conditions as sleep disorders, jet lag, pathologies that occur in advanced age.

In general, such screening procedures may involve using appropriate cells which express the HSCLOCK polypeptide or respond to HSCLOCK polypeptide of the present invention. Such cells include cells from mammals, yeast, Drosophila or *E. coli.* Cells which express the HSCLOCK polypeptide (or cell membrane containing the expressed polypeptide) or respond to HSCLOCK polypeptide are then contacted with a test compound to observe binding, or stimulation or inhibition of a functional response. The ability of the cells which were contacted with the candidate compounds is compared with the same cells which were not contacted for HSCLOCK activity.

The assays may simply test binding of a candidate compound wherein adherence to the cells bearing the HSCLOCK polypeptide is detected by means of a label directly or indirectly associated with the candidate compound or in an assay involving competition with a labeled competitor. Further, these assays may test whether the candidate compound results in a signal generated by activation of the HSCLOCK polypeptide, using detection systems appropriate to the cells bearing the HSCLOCK polypeptide. Inhibitors of activation are generally assayed in the presence of a known agonist and the effect on activation by the agonist by the presence of the candidate compound is observed.

Further, the assays may simply comprise the steps of mixing a candidate compound with a solution containing a HSCLOCK polypeptide to form a mixture, measuring HSCLOCK activity in the mixture, and comparing the HSCLOCK activity of the mixture to a standard.

The HSCLOCK cDNA, protein and antibodies to the protein may also be used to configure assays for detecting the effect of added compounds on the production of HSCLOCK mRNA and protein in cells. For example, an ELISA may be constructed for measuring secreted or cell associated levels of HSCLOCK protein using monoclonal and polyclonal antibodies by standard methods known in the art, and this can be used to discover agents which may inhibit or enhance the production of HSCLOCK (also called antagonist or agonist, respectively) from suitably manipulated cells or tissues.

The HSCLOCK protein may be used to identify membrane bound or soluble receptors, if any, through standard receptor binding techniques known in the art. These include, but are not limited to, ligand binding and crosslinking assays in which the HSCLOCK is labeled with a radioactive isotope (eg 125I), chemically modified (eg biotinylated), or fused to a peptide sequence suitable for detection or purification, and incubated with a source of the putative receptor (cells, cell membranes, cell supernatants, tissue extracts, bodily fluids). Other methods include biophysical techniques such as surface plasmon resonance and spectroscopy. In addition to being used for purification and cloning of the receptor, these binding assays can be used to identify agonists and antagonists of HSCLOCK which compete with the binding of HSCLOCK to its receptors, if any. Standard methods for conducting screening assays are well understood in the art.

Examples of potential HSCLOCK polypeptide antagonists include antibodies or, in some cases, oligonucleotides or proteins which are closely related to the ligands, substrates, receptors, enzymes, etc., as the case may be, of the HSCLOCK polypeptide, e.g., a fragment of the ligands, substrates, receptors, enzymes, etc.; or small molecules which bind to the polypetide of the present invention but do not elicit a response, so that the activity of the polypeptide is prevented.

Thus in another aspect, the present invention relates to a screening kit for identifying agonists, antagonists, ligands, receptors, substrates, enzymes, etc. for HSCLOCK polypeptides; or compounds which decrease or enhance the production of HSCLOCK polypeptides, which comprises:
(a) a HSCLOCK polypeptide, preferably that of SEQ ID NO:2;
(b) a recombinant cell expressing a HSCLOCK polypeptide, preferably that of SEQ ID NO:2;
(c) a cell membrane expressing a HSCLOCK polypeptide; preferably that of SEQ ID NO: 2; or
(d) antibody to a HSCLOCK polypeptide, preferably that of SEQ ID NO: 2.

It will be appreciated that in any such kit, (a), (b), (c) or (d) may comprise a substantial component.

PROPHYLACTIC AND THERAPEUTIC METHODS

This invention provides methods of treating abnormal conditions such as, sleep disorders, jet lag, pathologies that occur in advanced age, related to both an excess of and insufficient amounts of HSCLOCK polypeptide activity.

If the activity of HSCLOCK polypeptide is in excess, several approaches are available. One approach comprises administering to a subject an inhibitor compound (antagonist) as hereinabove described along with a pharmaceutically acceptable carrier in an amount effective to inhibit the function of the HSCLOCK polypeptide, such as, for example, by blocking the binding of ligands, substrates, receptors, enzymes, etc., or by inhibiting a second signal, and thereby alleviating the abnormal condition. In another approach, soluble forms of HSCLOCK polypeptides still capable of binding the ligand, substrate, enzymes, receptors, etc. in competition with endogenous HSCLOCK polypeptide may be administered. Typical embodiments of such competitors comprise fragments of the HSCLOCK polypeptide.

In still another approach, expression of the gene encoding endogenous HSCLOCK polypeptide can be inhibited using expression blocking techniques. Known such techniques involve the use of antisense sequences, either internally generated or separately administered. See, for example, O'Connor, *J Neurochem* (1991) 56:560 in *Oligodeoxynucleotides as Antisense Inhibitors of Gene Expression*, CRC Press, Boca Raton, Fla. (1988). Alternatively, oligonucleotides which form triple helices with the gene can be supplied. See, for example, Lee et al., *Nucleic Acids Res* (1979) 6:3073; Cooney et al., *Science* (1988) 241:456; Dervan et al., *Science* (1991) 251:1360. These oligomers can be administered per se or the relevant oligomers can be expressed in vivo.

For treating abnormal conditions related to an underexpression of HSCLOCK and its activity, several approaches are also available. One approach comprises administering to a subject a therapeutically effective amount of a compound which activates HSCLOCK polypeptide, i.e., an agonist as described above, in combination with a pharmaceutically acceptable carrier, to thereby alleviate the abnormal condition. Alternatively, gene therapy may be employed to effect the endogenous production of HSCLOCK by the relevant cells in the subject. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a subject for engineering cells in vivo and expression of the polypeptide in vivo. For overview of gene therapy, see Chapter 20, *Gene Therapy and other Molecular Genetic-based Therapeutic Approaches*, (and references cited therein) in Human Molecular Genetics, T Strachan and A P Read, BIOS Scientific Publishers Ltd (1996). Another approach is to administer a therapeutic amount of HSCLOCK polypeptides in combination with a suitable pharmaceutical carrier.

FORMULATION AND ADMINISTRATION

Peptides, such as the soluble form of HSCLOCK polypeptides, and agonists and antagonist peptides or small molecules, may be formulated in combination with a suitable pharmaceutical carrier. Such formulations comprise a therapeutically effective amount of the polypeptide or compound, and a pharmaceutically acceptable carrier or excipient. Such carriers include but are not limited to, saline, buffered saline, dextrose, water, glycerol, ethanol, and combinations thereof. Formulation should suit the mode of administration, and is well within the skill of the art. The invention further relates to pharmaceutical packs and kits comprising one or more containers filled with one or more of the ingredients of the aforementioned compositions of the invention.

Polypeptides and other compounds of the present invention may be employed alone or in conjunction with other compounds, such as therapeutic compounds.

Preferred forms of systemic administration of the pharmaceutical compositions include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if properly formulated in enteric or encapsulated formulations, oral administration may also be possible. Administration of these compounds may also be topical and/or localized, in the form of salves, pastes, gels and the like.

The dosage range required depends on the choice of peptide, the route of administration, the nature of the formulation, the nature of the subject's condition, and the judgment of the attending practitioner. Suitable dosages, however, are in the range of 0.1–100 $\mu$g/kg of subject. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide ex vivo, and for example, by the use of a retroviral plasmid vector. The cells are then introduced into the subject.

All publications, including but not limited to patents and patent applications, cited in this specification are herein incorporated by reference as if each individual publication were specifically and individually indicated to be incorporated by reference herein as though fully set forth.

SEQ ID NO:1

```
   1 AGCTGATTCTATCACATTGTAAGATGCCTTTGGATAATTCTACAGTCCTCTTAAATGAAT
  61 CTTTAGAACTTGGCAAGTCTCACTAGATACCTTCAATCATCATTTTGAGCTCAAAGAATT
 121 CTGAGACTTATGGTTGGTCATATAGAAGAGGACCTTGAACCTATAGTTTCCTGAAGAATC
 181 AGTTTAAAAGATCCAAGGAGTACAAAAGGAGAAGTACAAATGTCTACTACAAGACGAAAA
 241 CGTAGTATGTTATGTTGTTTACCGTAAGCTGTAGTAAAATGAGCTCGATTGTTGACAGAG
 301 ATGACAGTAGTATTTTTGATGGGTTGGTGGAAGAAGATGACAAGGACAAAGCGAAAAGAG
 361 TATCTAGAAACAAATCTGAAAAGAAACGTAGAGATCAATTTAATGTTCTCATTAAAGAAC
 421 TGGGATCCATGCTTCCTGGTAATGCTAGAAAGATGGACAAATCTACTGTTCTGCAGAAAA
 481 GCATTGATTTTTTACGAAAACATAAAGAAATCACTGCACAGTCAGATGCTAGTGAAATTC
 541 GACAGGACTGGAAACCTACATTCCTTAGTAATGAAGAGTTTACACAATTAATGTTAGAGG
 601 CTCTTGATGGTTTTTTTTAGCAATCATGACAGATGGAAGCATAATATATGTGTCTGAGA
 661 GTGTAACTTCATTACTTGAACATTTACCATCTGATCTTGTGGATCAAAGTATATTTAATT
 721 TTATCCCAGAAGGGGAACATTCAGAGGTTTATAAAATACTCTCTACTCATCTGCTGGAAA
 781 GTGATTCATTAACCCCAGAATATTTAAAATCAAAAAATCAGTTAGAATTCTGTTGTCACA
 841 TGCTGCGAGGAACAATAGACCCAAAGGAGCCATCTACCTATGAATATGTAAAATTTATAG
 901 GAAATTTCAAATCTTTAAACAGTGTATCCTCTTCAGCACACAATGGTTTTGAAGGAACTA
 961 TACAACGCACACATAGGCCATCTTATGAAGATAGAGTTTGTTTTGTAGCTACTGTCAGGT
1021 TAGCTACACCTCAGTTCATCAAGGAAATGTGCACTGTTGAAGAACCCAATGAAGAGTTTA
1081 CATCTAGACATAGTTTAGAATGGAAGTTTCTGTTTCTAGATCACAGGGCACCACCCATAA
1141 TAGGGTATTTGCCATTTGAAGTTCTGGGAACATCAGGCTATGATTACTATCATGTGGATG
1201 ACCTAGAAAATTTGGCAAAATGTCATGAGCACTTAATGCAATATGGGAAAGGCAAATCAT
1261 GTTATTATAGGTTCCTGACTAAGGGGCAACAGTGGATTTGGCTTCAGACTCATTATTATA
1321 TCACTTACCATCAGTGGAATTCAAGGCCAGAGTTTATTGTTTGTACTCACACTGTAGTAA
1381 GTTATGCAGAAGTTAGGGCTGAAAGACGACGAGAACTTGGCATTGAAGAGTCTCTTCCTG
1441 AGACAGCTGCTGACAAAAGCCAAGATTCTGGGTCAGATAATCGTATAAACACAGTCAGTC
1501 TCAAGGAAGCATTGGAAAGGTTTGATCACAGCCCAACCCCTTCTGCCTCTTCTCGGAGTT
1561 CAAGAAAATCATCTCACACGGCCGTCTCAGACCCTTCCTCAACACCAACCAAGATCCCGA
1621 CGGATACGAGCACTCCACCCAGGCAGCATTTACCAGCTCATGAGAAGATGGTGCAAAGAA
1681 GGTCATCATTTAGTAGTCAGTCCATAAATTCCCAGTCTGTTGGTTCATCATTAACACAGC
1741 CAGTGATGTCTCAAGCTACAAATTTACCAATTCCACAAGGCATGTCCCAGTTTCAGTTTT
1801 CAGCTCAATTAGGAGCCATGCAACATCTGAAAGACCAATTGGAACAACGGACACGCATGA
1861 TAGAAGCAAATATTCATCGGCAACAAGAAGAACTAAGAAAAATTCAAGAACAACTTCAGA
1921 TGGTCCATGGTCAGGGGCTGCAGATGTTTTGCAACAATCAAATCCTGGGTTGAATTTTG
1981 GTTCCGTTCAACTTTCTTCTGGAAATTCATCTAACATCCAGCAACTTGCACCTATAAATA
2041 TGCAAGGCCAAGTTGTTCCTACTAACCAGATTCAAAGTGGAATGAATACTGGACACATTG
2101 GCACAACTCAGCACATGATACAACAACAGACTTTACAGAGTACATCAACTCAGAGTCAAC
2161 AAAATGTACTGAGTGGGCACAGTCAGCAAACATCTCTACCCAGTCAGACACAGAGCACTC
2221 TTACAGCCCCACTGTATAACACTATGGTGATTTCTCAGCCTGCAGCCGGAAGCATGGTCC
2281 AGATTCCATCTAGTATGCCACAAAACAGCACCCAGAGTGCTGCAGTAACTACATTCACTC
2341 AGGACAGGCAGATAAGATTTTCTCAAGGTCAACAACTTGTGACCAAATTAGTGACTGCTC
```

-continued

```
2401 CTGTAGCTTGTGGGGCAGTCATGGTACCTAGTACTATGCTTATGGGCCAGGTGGTGACTG
2461 CATATCCTACTTTTGCTACACAACAGCAACAGTCACAGACATTGTCAGTAACGCAGCAGC
2521 AGCAGCAGCAGAGCTCCCAGGAGCAGCAGCTCACTTCAGTTCAGCAACCATCTCAGGCTC
2581 AGCTGACCCAGCCACCGCAACAATTTTTACAGACTTCTAGGTTGCTCCATGGGAATCCCT
2641 CAACTCAACTCATTCTCTCTGCTGCATTTCCTCTACAACAGAGCACCTTCCCTCAGTCAC
2701 ATCACCAGCAACATCAGTCTCAGCAACAGCAGCAACTCAGCCGGCACAGGACTGACAGCT
2761 TGCCCGACCCTTCCAAGGTTCAACCACAGTAGCACACGTGCTTCCTCTCTTGACATCAAG
2821 GGAGGAAGGGGATGGCCCATTAAGAGTTACTCAGATGACCTGAGGAAAGGAGGGAAAGTT
2881 CCAGCAGTTTCATGAGATGCAGTATTGAGTGTTCTAGTTCCTGGAATTAGTTGGCAGAGA
2941 AAATGCTGCCTAGTGCTACAGATGTACATTAAATACCAGCCAGCAGGAGGTGATCATAGG
3001 GGCACAGCCAGTTCTGACAGTGTTTTAGGTGCCTGGATATTTTTGATGGAAAAGAATA
3061 TATTGCCAAATATTAAGAAGCTCAGCTATGAAATGACCTCCAGGGAATCAGAAAGGCACT
3121 AATGATGTTAGTAACTTTTAGTGGTTCTGTGCCTCTTATCAAGTGTTACAGAGGACATAC
3181 CACTGCCATGTCAGGGGTTTGCTTACAGTGATGCCATGAAGACAGTCCAGTAGACTTGGT
3241 AGCGACCCCCTCCCCCAACCCCTCTCCCTTTTCAGATAATGATGGAACAGTAATTACTTT
3301 CAGAATGTTGTGTGGGTTCAAATTCTCTATGTACAGATGATGTAAAAATATGTATATGTC
3361 TAGATAAAAGGAGAGAAAGCAAAACATTTTGTATGCTGCATGAAAGCGTTATCTCTTCCT
3421 TACAGGTGTGAGCACCTTTCCTGAAATTCTGACACCATGTGCAAACTGATCCATCCTGTT
3481 TTTCCTTTTGTTTACAACACAGTAGTGTTCTGTTCACTTTTCCGGGGCACAAGTTTTTTT
3541 GTTCATACTTTGGCTGTGATGTCACAGTTTGTTCAGTGAGGTATGATGTGCTGCTGGGAA
3601 TGGATTTTTTTTTTCAGGTTAAATTATTGATACAACAGGATTTTCAAGTTATTCAGAAA
3661 TATCCCTCATTTCATTATTTTTCAATTATGTTTGAAAATAGGATTTGCACTGCTTTATTT
3721 TAGGTGGCTGGGAGTTTTGATTGCATATTTTGTTATAGTTCATAGTTGGAAATATTTGCG
3781 TAAATGGTTTTCAACAAGCCTGAAAGTAATTTCAAGAATGTTTCAGTTATAGAGGTAAAA
3841 TTTGCACACAAAACATCTTAGGCACTTTTTAACATTCTCAATCATGGGAATTTTAACTTT
3901 TGGGATTTGTTGAAATCTTTTTTATTATCCTTCACAATTTCAATGCTTCTTTTAGTCAGA
3961 AATGATTCAGGGTTATTTGAGGGGAAAAAACCCCATAGTGCCTTGATTTTAATTCAGGTG
4021 ATAACTCACCATCTTGAAGTCATTGTCCGGTTTCCGTAGCAGTTTTGAAACCTTAGTACC
4081 TTTTTAACAGCATGTGGGTGTCAGTGTCATTATTAGTCTCCTAATAAGTTCCTCTGAAGA
4141 CTGCTATCAGTCTCTTGGACTGGAGTTACAAATAATTTAGAAATAAAAGATGATAACCTA
4201 ACACTATCATAGTTATTAATGTGATCCTAAAATTGTTTCCTAAATCAGCATTTTTCTTTA
4261 GTCATTTAAGAATTTACCAGAAATATTTGCTCAATATGATCTTGATATTCCTACAAAGAA
4321 AAAAGAAGGGGTAGGGATTTGGCTATGCCTTCACTACAACATTAGAATATTGTAACTCAC
4381 ATGCCTTCTAAACGTGAACTAAGATTTCCTTTGGCAATATCATATTCTAAAAGTAATAAA
4441 TTCCAATACAAGTTACATACATTTAAAAAACATTTTACAGATTTTATGGTACTAATGAAA
4501 TTTACAGTGATAGAACAAAAGAGGATTAGTAGAAAATACATTATTAGAATATAAAAAATG
4561 TTATTACTGAGGAAAGGGAGGAGAGGACAAGTGTAATAAATCAAAATTGACCTCAAAAGA
4621 AAATGTGTAACAGAGTTGAGGTTGTTAAAACAGAAAAGGTTCTGAATAATGAAGATTAAC
4681 CTAATGCAGAATTGCTAGGTAAAGAGGTCAGGGGAATGCTAAGCCAGTTCTTAAGACTTC
4741 TCTGTCCTCTGCTTTGCTGTTATCCTTAAGGCATATACTTTGTCTTTCTGCAGAAAATTC
```

-continued

```
4801 TACCTGGCTACAATTACTTTGAACATTAATGTTGAAAAGAAAACAACCAAAGAAAATTG

4861 GTACTTACCCTTCTACAAAAGAAGTGTGACTAGATATCAATCAGTAATTAACATATCAAG

4921 GAGCTCTTCTAGCTAAATGACCATCCAGTAGAGATTTCCCACATTCCCATGAATATCAAG

4981 AATAGTTGTCAGAATATGTATGTACCTGAGCATATGTACACAGACAAGGGGGATGTTGTG

5041 GAATATGGCAATAGCATTGTTCTTCTCCCCTTTCAAATTGCCTTTCTTGACCTTATGCCA

5101 TTCCATATATATCTGAGTTGTGCCTCATTTATTTATTGGCAATACCTAGTGATACGGATT

5161 TAGCTAACAAAAGATATGAAGAACTATTATATTGAGGCCTGTCCTCTACATACCACACTT

5221 AAAAGATGGTGAACTGTGAGTACTACTTAGGTTGACAGCAACAAAGCATAAGACAAGCCC

5281 CAGGTAAACGTCTAAACTGTTTACTCACATTGTCCTACTCCAGCCCCTTCAATTATTTCC

5341 CATCTCCACAAATAGTCGGGGAAAAAATTAAAATTTTCCTTTATGATTCTTACTGTTCT

5401 TCGCAGCTCATCTTTTCCTGCTTAGAATTAACCATTGCTAATTTAAAGGAGCAGCTAGCT

5461 GCTTTTCTGTCAGTCTGAAGCGTAGTAGTGGAAGAGGTAGTAAGCACCAGCTGCCTCTTT

5521 GCTGCTTTGTTTTCCTCCTGATTCTCTTAAATTTGGGTTGCAAAGCTATCCCGCCCCCCA

5581 CCCTGCCCCATGAAACTTGAGCATTCAAATGAAGATTCAGCAGTGTCTGTTCTTCATTTC

5641 TATAGCCAAAGCTGTTAGTTAAAATCCCAAATCTATAGCATTTAAAGATACCAAATAGAA

5701 ACACCTTCCAGCTTT  5715
```

SEQ ID NO:2
```
  1 MLFTVSCSKMSSIVDRDDSSIFDGLVEEDDKDKAKRVSRNKSEKKRRDQFNVLIKELGSM

61 LPGNARKMDKSTVLQKSIDFLRKHKEITAQSDASEIRQDWKPTFLSNEEFTQLMLEALDG

121 FFLAIMTDGSIIYVSESVTSLLEHLPSDLVDQSIFNFIPEGEHSEVYKILSTHLLESDSL

181 TPEYLKSKNQLEFCCHMLRGTIDPKEPSTYEYVKFIGNFKSLNSVSSSAHNGFEGTIQRT

241 HRPSYEDRVCFVATVRLATPQFIKEMCTVEEPNEEFTSRHSLEWKFLFLDHRAPPIIGYL

301 PFEVLGTSGYDYYHVDDLENLAKCHEHLMQYGKGKSCYYRFLTKGQQWIWLQTHYYITYH

361 QWNSRPEFIVCTHTVVSYAEVRAERRRELGIEESLPETAADKSQDSGSDNRINTVSLKEA

421 LERFDHSPTPSASSRSSRKSSHTAVSDPSSTPTKIPTDTSTPPRQHLPAHEKMVQRRSSF

481 SSQSINSQSVGSSLTQPVMSQATNLPIPQGMSQFQFSAQLGAMQHLKDQLEQRTRMIEAN

541 IHRQQEELRKIQEQLQMVHGQGLQMFLQQSNPGLNFGSVQLSSGNSSNIQQLAPINMQGQ

601 VVPTNQIQSGMNTGHIGTTQHMIQQQTLQSTSTQSQQNVLSGHSQQTSLPSQTQSLTAP

661 LYNTMVISQPAAGSMVQIPSSMPQNSTQSAAVTTFTQDRQIRFSQGQQLVTKLVTAPVAC

721 GAVMVPSTMLMGQVVTAYPTFATQQQQSQTLSVTQQQQQQSSQEQQLTSVQQPSQAQLTQ

781 PPQQFLQTSRLLHGNPSTQLILSAAFPLQQSTFPQSHHQQHQSQQQQQLSRHRTDSLPDP

841 SKVQPQ  846
```

---

What is claimed is:

1. An expression system comprising a polynucleotide capable of producing a HSCLOCK peptide comprising the amino acid sequence as set forth in SEQ ID NO:2 when said expression system is present in a compatible host cell.

2. A process for producing a recombinant host cell comprising transforming or transfecting a cell with the expression system of claim 1 such that the host cell, under appropriate culture conditions, produces a polypeptide comprising the amino acid sequence of SEQ ID NO:2.

3. A recombinant host cell produced by the process of claim 2.

4. A membrane of a recombinant host cell of claim 3 expressing a polypeptide comprising the amino acid sequence of SEQ ID NO:2.

5. A process for producing a polypeptide comprising culturing a host cell of claim 3 under conditions sufficient for the production of said polypeptide and recovering the polypeptide from the culture.

* * * * *